US009643325B2

(12) United States Patent
Berkelman et al.

(10) Patent No.: US 9,643,325 B2
(45) Date of Patent: *May 9, 2017

(54) SYSTEM FOR POSITIONING ON A PATIENT AN OBSERVATION AND/OR INTERVENTION DEVICE (71) Applicant: Université Grenoble Alpes, Saint Martin d'Heres (FR)

(72) Inventors: Peter Berkelman, Honolulu, HI (US); Philippe Cinquin, Saint Nazaire les Eymes (FR); Alain Jacquet, Moretel de Mailles (FR); Jean Arnault, Saint Nazaire les Eymes (FR)

(73) Assignee: UNIVERSITÉ GRENOBLE ALPES, Saint Martin (FR)

( * ) Notice: Subject to any disclaimer, the term of this patent is extended or adjusted under 35 U.S.C. 154(b) by 588 days.

This patent is subject to a terminal disclaimer.

(21) Appl. No.: 14/087,724

(22) Filed: Nov. 22, 2013

(65) Prior Publication Data
US 2014/0076088 A1 Mar. 20, 2014

Related U.S. Application Data (62) Division of application No. 13/172,700, filed on Jun. 29, 2011, now Pat. No. 8,591,397, which is a division
(Continued)

(30) Foreign Application Priority Data

May 13, 2002 (FR) ..................................... 02 05848

(51) Int. Cl.
A61B 19/00 (2006.01)
B25J 18/00 (2006.01)
(Continued)

(52) U.S. Cl.
CPC ............ *B25J 18/00* (2013.01); *A61B 17/3403* (2013.01); *A61B 90/50* (2016.02); *A61B 34/20* (2016.02);
(Continued)

(58) Field of Classification Search
CPC .......... B25J 18/00; A61B 34/20; A61B 34/70; A61B 90/50; A61B 17/3403; A61B 90/11;
(Continued)

(56) References Cited

U.S. PATENT DOCUMENTS 5,201,742 A 4/1993 Hasson
6,030,402 A 2/2000 Thompson et al.
(Continued)

FOREIGN PATENT DOCUMENTS

DE 4307876 C1 7/1994
DE 19647516 A1 5/1998
(Continued)

OTHER PUBLICATIONS http://www.merriam-webstercom/dictionary/cable, Dated Oct. 6, 2010.

Primary Examiner — Katrina Stransky
(74) Attorney, Agent, or Firm — Howard IP Law Group, PC (57) ABSTRACT The present invention relates to a system for positioning with respect to a patient's body an observation and/or intervention device having a portion penetrating into the patient's body comprising a base disposed over the patient's body; a means for supporting the device formed of a first portion movably assembled on the base according to a connection with one degree of freedom, and of a second portion movably assembled on the first portion according to a connection with one degree of freedom and connected to
(Continued)

the device; and means for actuating the first portion with respect to the base, and the second portion with respect to the first portion, in which the base surrounds at a distance at least partially the device, said device being detachably connected to the second portion to enable removal of the positioning system while leaving in place the device.

19 Claims, 5 Drawing Sheets

Related U.S. Application Data of application No. 10/514,353, filed as application No. PCT/FR03/01455 on May 13, 2003, now abandoned.

(51) Int. Cl.

| | | |
|---|---|---|
| *A61B 17/34* | (2006.01) | |
| *A61B 90/50* | (2016.01) | |
| *A61B 17/00* | (2006.01) | |
| *A61B 34/20* | (2016.01) | |
| *A61B 34/00* | (2016.01) | |
| *A61B 90/00* | (2016.01) | |
| *A61B 90/11* | (2016.01) | |

(52) U.S. Cl.
CPC ............. *A61B 34/70* (2016.02); *A61B 90/11* (2016.02); *A61B 90/361* (2016.02); *A61B 2017/00398* (2013.01); *A61B 2017/3407* (2013.01); *A61B 2017/3409* (2013.01); *Y10S 901/19* (2013.01); *Y10T 74/20305* (2015.01)

(58) Field of Classification Search
CPC ........ A61B 90/361; A61B 2017/00398; A61B 2017/3407; A61B 2017/3405; A61B 2017/3409
USPC .......................................................... 606/130
See application file for complete search history.

(56) References Cited

U.S. PATENT DOCUMENTS

| | | |
|---|---|---|
| 6,351,662 B1 | 2/2002 | Franck et al. |
| 6,997,866 B2 | 2/2006 | Payandeh et al. |
| 8,591,397 B2 | 11/2013 | Berkelman et al. |
| 2001/0053879 A1 | 12/2001 | Mills et al. |
| 2002/0010479 A1 | 1/2002 | Skakoon et al. |
| 2003/0229338 A1 | 12/2003 | Irion et al. |
| 2004/0122446 A1 | 6/2004 | Solar |

FOREIGN PATENT DOCUMENTS

| | | |
|---|---|---|
| FR | 2796263 | 1/2001 |
| WO | 9420035 | 9/1994 |
| WO | 9421188 | 9/1994 |
| WO | 0236060 A2 | 5/2002 |

SYSTEM FOR POSITIONING ON A PATIENT AN OBSERVATION AND/OR INTERVENTION DEVICE

CROSS-REFERENCE TO RELATED APPLICATIONS

This application is a divisional application of U.S. patent application Ser. No. 13/172,700, filed Jun. 29, 2011, which claims priority to U.S. patent application Ser. No. 10/514,353, filed on May 13, 2003, which claims the benefit of French Application No. 02/05848, filed May 13, 2002 and Intl. Application No. PCT/FR03/01455, filed May 13, 2003, the entire contents of which are incorporated by reference herein.

FIELD OF THE INVENTION

The present invention relates to a system for positioning on a patient an observation and/or intervention device having a portion penetrating into the patient's body. It for example applies to medical analysis systems, such as endoscopic systems, and it will more specifically be described in the case of a use of an endoscope in a laparoscopy.

BACKGROUND

In such a type of operation, an endoscope formed of a thin optical tube is inserted into the patient's abdomen through a small incision performed at the level of the patient's abdomen. The optical tube is generally connected to an external video camera. Other incisions may be performed to introduce surgical instruments handled by a surgeon. The endoscope is used to visualize the patient's internal organs and the surgical instruments. Since the surgeon generally has both hands occupied by the surgical instruments, an assistant is necessary to maintain the endoscope in a desired position.

Robotic systems have been developed to handle the endoscope instead of the assistant. Such systems are generally formed of massive, complex, and expensive robots comprising a base attached to the ground and an arm handling the endoscope. In the limited space of an operation table, the base of such a robot takes up a considerable place next to the patient. Further, the robot's arm maintaining the endoscope may hinder the access to the patient's abdomen.

It is thus desirable to provide a system for positioning on a patient an observation and/or intervention instrument taking up a small volume to limit the space required in the operation theatre and clear the access to the patient as much as possible.

International patent application WO0105319 assigned to the Universite Joseph Fourier describes, in an embodiment, a system for positioning an observation and/or intervention device, for example, an endoscope. The system comprises a mount placed on the patient's body, supporting a trocar in which the observation and/or intervention device slides, the trocar being likely to pivot with respect to the mount. An actuator assembly controls the trocar movement with respect to the mount. It may be formed of pneumatic or hydraulic actuators, each actuator being directly connected to the mount and to the trocar. It may also be formed of cables. Each cable then extends between the trocar and a guide attached on the mount, and is driven at its free end by an actuator placed at a distance from the patient.

A disadvantage of such a system is the difficulty to impose significant movements to the trocar. Indeed, in the case where the actuators are placed directly on the mount, the volume taken up by the actuators limits the trocar movements. In the case where the actuators are placed at a distance from the patient, the trocar movements are obtained by the application of tractions of different amplitudes on the cables connected to the trocar. A difficulty then results, in large movements, from the high flexion angles imposed to the cables at the level of the guides. This may result in a fast deterioration of the cables. Further, with such a system, the forces exerted by the cables or the actuators on the trocar are the origin of a pressure exerted by the trocar on the patient's abdomen that may be undesirable. Another disadvantage of such a system is that it is generally not possible to remove the positioning system while leaving in place the trocar and the observation and/or intervention devices.

SUMMARY

The present invention provides a system, taking up a small volume, for positioning on a patient's body an observation and/or intervention device having a portion penetrating into the patient's body, enabling obtaining significant movements of the observation device and enabling removal of the positioning system while leaving in place the observation and/or intervention device.

The present invention also provides a positioning system limiting the application of pressure forces on the patient's abdomen.

To achieve these objects, the present invention provides a system for positioning with respect to a patient's body an observation and/or intervention device having a portion penetrating into the patient's body comprising a base laid on the patient's body; a means for supporting the device formed of a first portion movably assembled on the base according to a connection with one degree of freedom, and of a second portion movably assembled on the first portion according to a connection with one degree of freedom and connected to the device; and means for actuating the first portion with respect to the base, and the second portion with respect to the first portion, in which the base surrounds at a distance at least partially the device and in which the device is detachably connected to the second portion to enable removal of the positioning system with respect to the device while leaving in place the device with respect to the patient's body.

According to an embodiment of the present invention, the base delimits a circular opening around the device and the first portion is a mobile ring with an axis substantially perpendicular to the patient's body and with an inner diameter substantially corresponding to the circular opening, the mobile ring being rotatably assembled on the base around its axis.

According to an embodiment of the present invention, the second portion comprises a head connected to the device prolonging at least in an arm pivotally assembled on the mobile ring along an axis substantially tangent to the patient's body.

According to an embodiment of the present invention, the first portion comprises a semi-circular rail having its ends pivotally assembled on the base along an axis substantially tangent to the patient's body.

According to an embodiment of the present invention, the second portion comprises a carriage slidably assembled on the rail and connected to the device.

According to an embodiment of the present invention, the device is movably assembled on the second portion according to a connection with one degree of freedom.

According to an embodiment of the present invention, the motions of the first and second portions are controlled by cables driven by actuators located at a distance from the patient.

According to an embodiment of the present invention, the rotating motion of the mobile ring with respect to the base is controlled by an actuator attached to the mobile ring, the actuator extending to be substantially parallel to the mobile ring axis.

According to an embodiment of the present invention, the pivoting motion of the arm with respect to the mobile ring is controlled by an actuator attached to the second portion and extending to be substantially parallel to the pivoting axis of the arm with respect to the mobile ring.

According to an embodiment of the present invention, the device extends substantially longitudinally along a direction perpendicular to the pivoting axis of the arm with respect to the mobile ring and the device is movably assembled with respect to the second portion, to slide along said direction, the device sliding with respect to the second portion being controlled by an actuator attached to the second portion and extending to be substantially parallel to the pivoting axis of the arm with respect to the mobile ring.

BRIEF DESCRIPTION OF THE DRAWINGS

The foregoing objects, features, and advantages, as well as others of the present invention will be discussed in detail in the following non-limiting description of specific embodiments in connection with the accompanying drawings, among which.

DETAILED DESCRIPTION

Figure 1A:
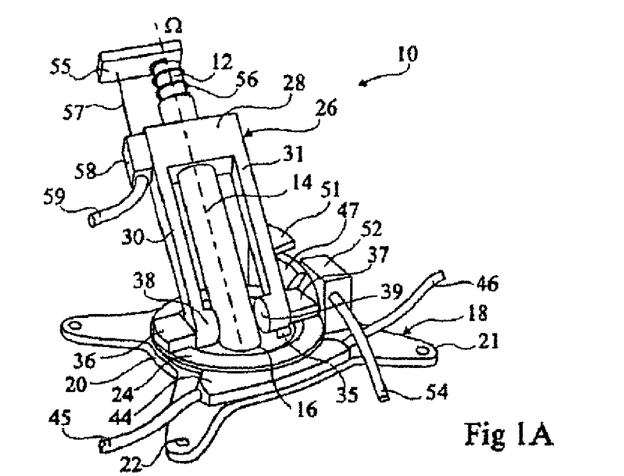
FIG. 1A shows a perspective view of a first embodiment of a positioning system according to the present invention.
Figure 1B:
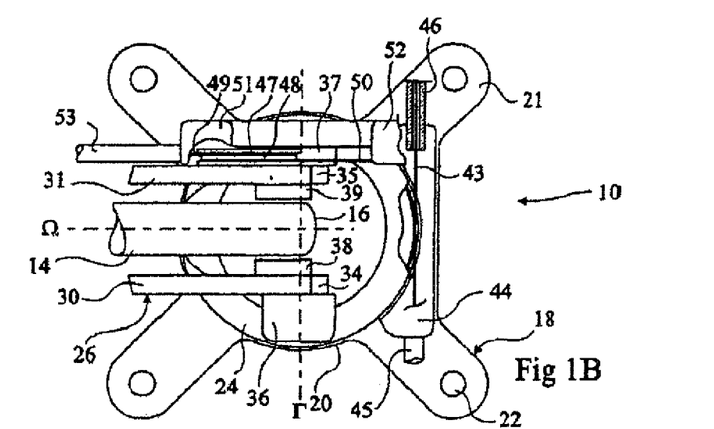
FIG. 1B shows a partial top view with a partial cross-section view of the system of FIG. 1A.
Figure 1C:
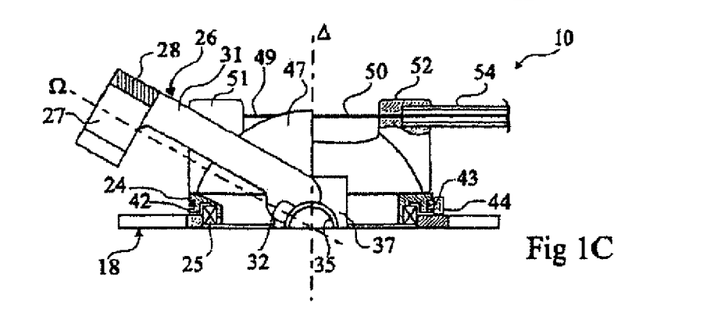
FIG. 1C shows a partial lateral cross-section view of the system of FIG. 1A.

FIGS. 1A to 1C show a first embodiment of a system 10 for positioning an endoscope 12 placed in a trocar 14, endoscope 12 and trocar 14 penetrating into a patient's abdomen through a small incision 16. Endoscope 12 has the aspect of a cylindrical tube of axis $\Omega$ of a length of some forty centimeters and of a diameter of a few centimeters. In FIG. 1B, a portion only of trocar 14 is shown. In FIG. 1C, only axis $\Omega$ of endoscope 12 is shown. A camera, not shown, is attached to the end of endoscope 12 external to the abdomen.

System 10 comprises a substantially planar base 18 comprising a planar ring-shaped central portion 20, surrounding incision 16, from which four arms 21 extend. A cylindrical opening 22 is formed at the end of each arm 21. Openings 22 may be used to maintain base 18 on the patient's body via straps, cables, etc. attached to the table on which the patient is laid or directly attached to the patient. Base 18 may also be glued on the patient's abdomen.

Central annular portion 20 supports a mobile ring 24 of axis $\Delta$ substantially perpendicularly to the plane tangent to the abdomen at the level of incision 16. Mobile ring 24 is rotatably assembled around axis $\Delta$ on central portion 20 via a bearing 25.

A stirrup 26 is pivotally assembled on mobile ring 24 according to an axis $\Gamma$ substantially perpendicular to axis $\Delta$, and substantially comprised in the plane tangent to the abdomen at the level of incision 16. Stirrup 26 comprises a head 28 on which is attached trocar 14 by any known attachment means, which enables simple and fast connection and separation of trocar 14 and of head 28. Said means will for example be flexible tongues 27. The inner diameters of mobile ring 24 and of ring-shaped central portion 20 are selected to enable removal of system 10 during an intervention without displacing trocar 14, or to enable removal of trocar 14 from the patient's abdomen without displacing system 10. Head 28 prolongs in two arms 30, 31, each comprising at one end a sliding surface 32, corresponding to a cylindrical portion, likely to slide on a profile 34, 35 shaped as a half-cylinder of axis $\Gamma$. Each profile 34, 35 moves along with a base 36, 37 attached on ring 24, for example, by screwing. Each arm 30, 31 comprises at its free end a cap 38, 39 (not shown in FIG. 1C) which forms with sliding surface 32 of the associated arm 30, 31 a housing receiving profile 34, 35.

Mobile ring 24 comprises on its external cylindrical wall a groove 42 receiving a cable 43. A guide 44 assembled on base 18 receives the ends of two sheaths 45, 46 in which cable 43 slides. Guide 44 is arranged on base 18 so that cable 43, as it comes out of one of sheaths 45, 46, is tangent to groove 42 of mobile ring 44. The ends of cable 43 are connected to the ends of a rack (not shown) meshing in with the output shaft of an electric motor. The displacement of cable 43 by the motor rotates ring 24 with respect to central annular portion 20 around axis $\Delta$.

A pulley sector 47, substantially corresponding to a cylindrical sector, is attached to one of arms 31 of stirrup 26. A groove 48 is formed on the lateral wall, corresponding to a cylinder portion of pulley sector 47. Groove 48 receives two cables 49 and 50, each cable 49, 50 being attached to an opposite end of groove 48. The other ends of cables 49, 50 are connected to the ends of a rack (not shown) meshing in with the output shaft of an electric motor. Two supports 51, 52 are attached to mobile ring 24 and each receives the end of a sheath 53, 54 in which one of cables 49, 50 slides. Supports 51, 52 are arranged so that cables 49, 50, as they come out of sheaths 53, 54 are substantially tangent to pulley sector 47. When the electric motor displaces the rack, a traction is exerted on one of cables 49, 50, and a thrust is exerted on the other cable 49, 50. Cables 49, 50 displace pulley sector 47 and, accordingly, stirrup 26. The sliding surfaces 32 of arms 30, 31 then slide on profiles 34, 35 so that stirrup 26 generally pivots with respect to axis $\Gamma$.

Endoscope 12 is assembled to freely slide along axis $\Omega$ in trocar 14. A hold element 55 is attached to endoscope 12. A compression spring 56 bears at one end against hold element 55 and at the opposite end against trocar 14. A cable 57 is connected at one end to hold element 55 and at its opposite end to a rack (not shown) meshing in with the output shaft of an electric motor. A guide 58 attached on head 28 of stirrup 26 receives the end of a protection sheath 59 in which cable 57 slides. A traction on cable 57 makes endoscope 12 slide in trocar 14 along axis Ω and compresses spring 56. When cable 57 is released, spring 56 relaxes and brings endoscope 12 back to an idle position. Hold element 55 can easily be removed from endoscope 12 to enable removal of endoscope 12 from trocar 14, for example, to clean its lens, or to replace it with another endoscope having a different length or viewing cone.

The three motors and the racks are for example arranged in a package distant from the patient. The motor control may be performed in any known fashion and will not be detailed hereafter. It may for example be a vocal control, a manual control by lever or buttons, a foot control, etc. The motor control may be performed in open or closed loop. For example, system 10 may also comprise a location means to detect the position and the orientation of incision 16, of endoscope 12, and of an intervention instrument handled by the surgeon. The location means may be connected to a calculator capable of controlling motors. The endoscope is then displaced to, for example, transmit an image permanently following the end of the intervention instrument.

The motors are preferably clutch releasable to enable the surgeon to manually displace positioning system 10.

Cables 43, 57 and cable assembly 49, 50 each control a degree of freedom of endoscope 12. Cables 43, 49, 50, 57 are arranged not to undergo significant flexion angles. In particular, pulley sector 47 has a sufficiently large radius, preferably greater than 50 mm, to limit the curvature of cables 49, 50. This enables preventing fast deterioration of cables 43, 49, 50, 57.

Base 18 and stirrup 26 may be made of steel to increase their durability and ease their sterilization. Cables 43, 49, 50, 57 may be formed of a material covered with Teflon and placed in Teflon sheaths 45, 46, 53, 54, 59.

Figure 2A:
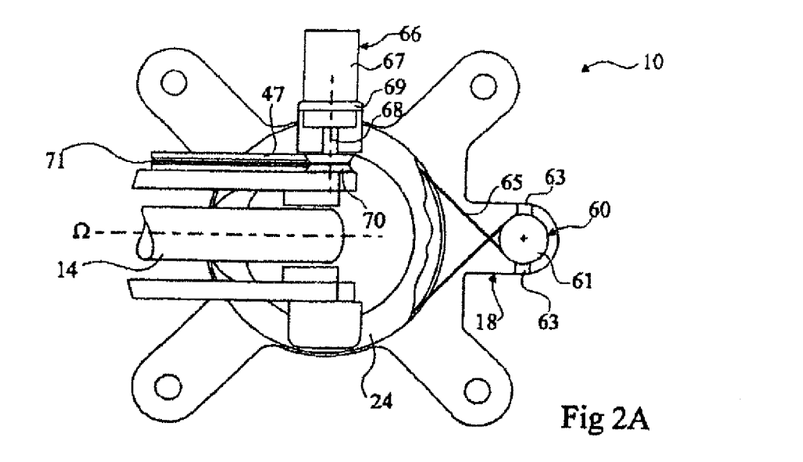
FIG. 2A shows a partial top view with a partial cross-section view of an alternative of the system according to the first embodiment.
Figure 2B:
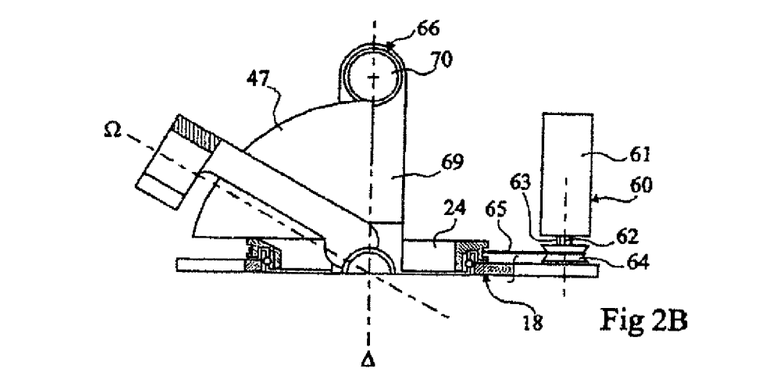
FIG. 2B shows a partial lateral cross-section view of the system of FIG. 2A.

FIGS. 2A and 2B are similar, respectively, to FIGS. 1B and 1C and show an alternative of positioning system 10 according to the first embodiment. Only the differences with respect to the first embodiment will be described.

According to this alternative, the electric motors driving the actuating cables are directly arranged at the level of positioning system 10. The motors are arranged to hinder as little as possible the movements of endoscope 12. For example, a first motor 60, comprising a cylindrical package 61 and an output shaft 62, is assembled on a support 63 connected to base 18 so that output shaft 62 substantially extends along an axis parallel to axis Δ. Output shaft 62 rotates a pulley 64. Pulley 64 is connected to mobile ring 24 by a cable 65 to drive mobile ring 24 similarly to the first embodiment.

A second motor 66, comprising a cylindrical package 67 and an output shaft 68, is assembled on a support 69 connected to mobile ring 24 so that output shaft 68 extends substantially along an axis perpendicular to axes Δ and Ω. Output shaft 68 rotates a pulley 70. Pulley 70 is connected to pulley sector 47 by a cable 71 to drive pulley sector 47 similarly to the first embodiment. The supply and control means of motors 60, 66 are not shown. Motors 60 and 66 may be controlled by any conventional device. In particular, packages 61, 67 may comprise supply means and remote-control means. The sliding of endoscope 12 in trocar 14 may also be controlled by a third motor (not shown) directly placed at the level of hold element 55.

The present alternative of the first embodiment enables completely freeing the patient's abdomen during the surgical intervention.

Figure 3A:
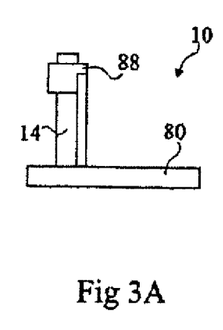
FIG. 3A shows a very simplified side view of a second embodiment of the system according to the present invention.
Figure 3B:
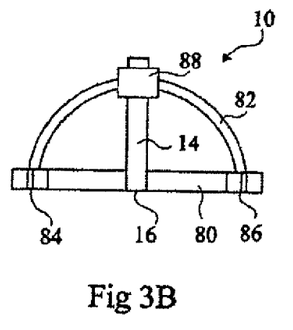
FIG. 3B shows a front view of the system of FIG. 3A.
Figure 3C:
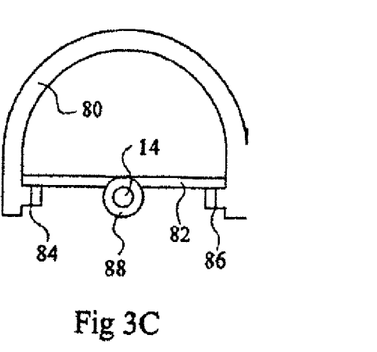
FIG. 3C shows a top view of the system of FIG. 3A.

FIGS. 3A to 3C very schematically show a second embodiment of system 10 for positioning trocar 14 in which the endoscope (not shown) slides, the trocar and the endoscope penetrating into the patient's abdomen through incision 89.

According to the second embodiment, system 10 comprises a "C"-shaped base 80 resting on the patient's abdomen. A semi-circular rail 82 is pivotally assembled on base 80 around an axis substantially tangent to the patient's abdomen. The two ends of rail 82 are substantially connected to the two ends of base 80 by two pivotal connections 84, 86. A carriage 88 is slidably assembled on rail 82. Carriage 88 supports trocar 14.

The means for controlling the sliding of the endoscope in trocar 14 are not shown in FIGS. 3A to 3C and may be identical to those of the first embodiment.

The sliding of carriage 88 on rail 82, and the pivoting of rail 82 with respect to base 80, may be controlled by cable driven by actuators placed at a distance from the patient as for the first embodiment, or by directly arranging the actuators at the level of positioning system 10 as for the previously-described alternative of the first embodiment.

According to an alternative of the present invention, the rotating motions of endoscope 12 in trocar 14 around its axis Ω may also be controlled by an actuator.

According to the second embodiment, the removal of the positioning system is eased by the fact that base 80 is "C" shaped.

Figure 4A:
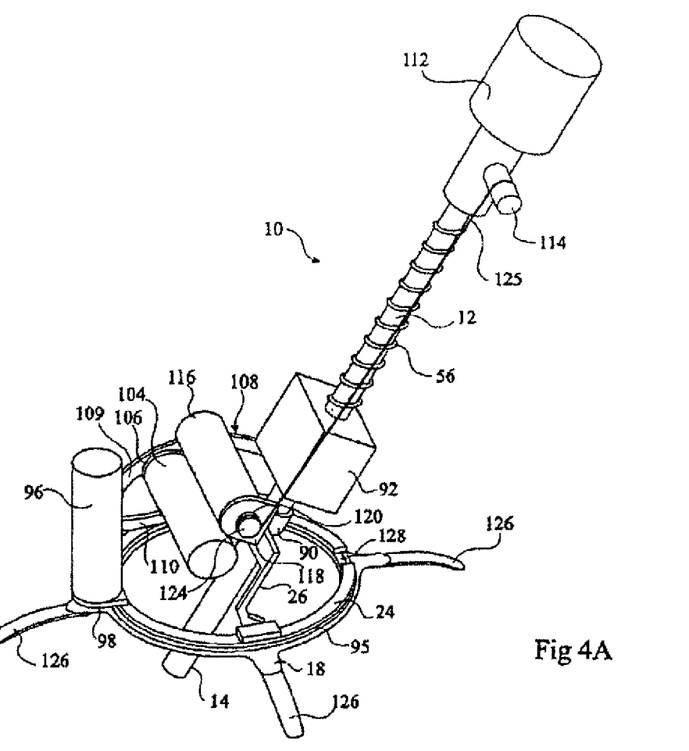
FIG. 4A shows a perspective view of an alternative of the first embodiment of a positioning system according to the present invention.
Figure 4B:
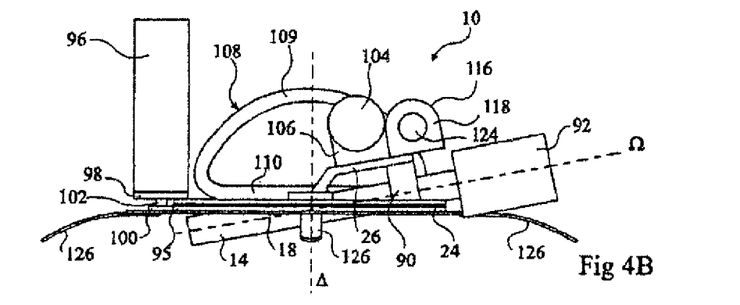
FIGS. 4B and 4C show side views of the system of FIG. 4A at two different positions.
Figure 4C:
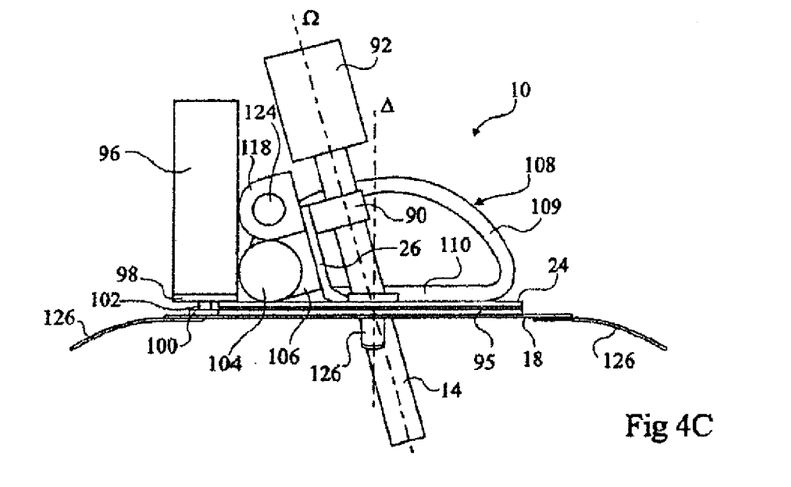
Figure 4D:
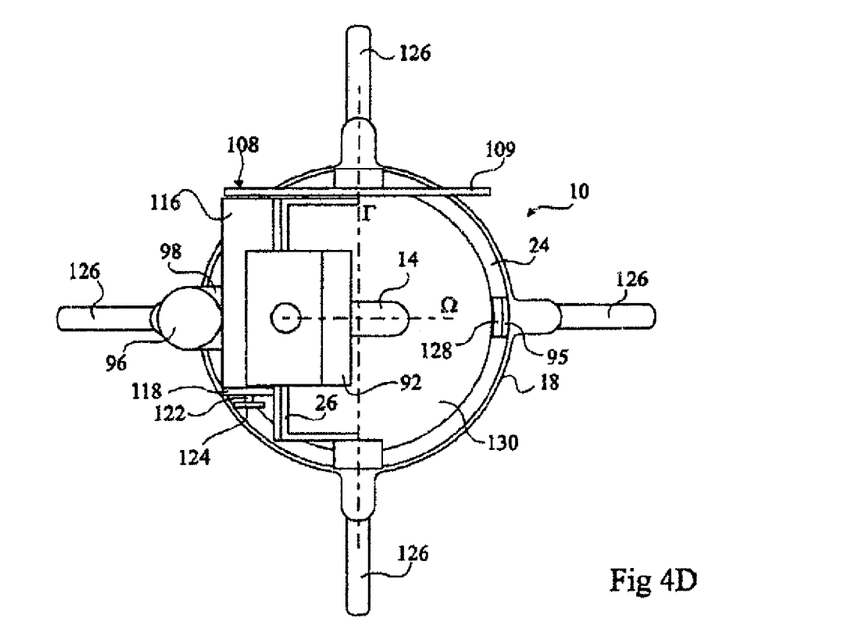
FIG. 4D shows a top view of the system of FIG. 4C.

FIGS. 4A to 4D show views of an alternative of positioning system 10 according to the first embodiment. In FIGS. 4A to 4D, the incision made on the patient for the placing of endoscope 12 has not been shown. In FIGS. 4B to 4D, only axis Ω of endoscope 12 is shown.

According to the present alternative of the first embodiment, trocar 14 is maintained on stirrup 26 by a mounting flange 90, for example, screwed on stirrup 26. Trocar 14 comprises a protrusion 92 located on the side of mounting flange 90 opposite to ring-shaped base 18. Protrusion 92 may represent handles, tightness valves, connectors, etc. A fixed ring 95 is arranged between ring-shaped base 18 and mobile ring 24. Fixed ring 95 forms one piece with base 18. Mobile ring 24 is rotatably assembled on fixed ring 95. Fixed ring 95 comprises a peripheral toothing (shown in FIG. 4E) on its external lateral surface.

Figure 4E:
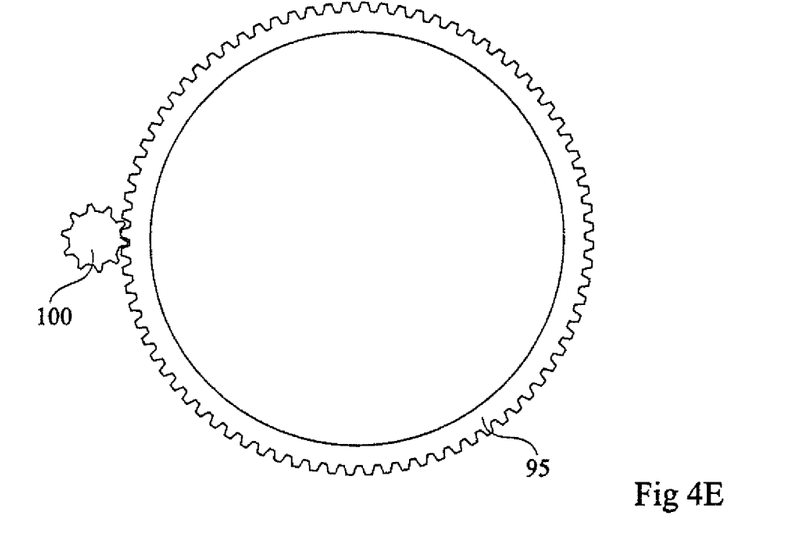
FIGS. 4E and 4F show top and side views, respectively, of parts of the system of FIG. 4A.

A first electric motor 96, intended to rotate mobile ring 24 with respect to fixed ring 95, is assembled to move along with mobile ring 24 via a stage 98. First motor 96 is controlled and supplied by means not shown, for example, by electric wires. A toothed wheel 100, shown in FIG. 4E, is arranged at the end of shaft 102 of first motor 96. Shaft 102 is substantially parallel to axis Δ of mobile ring 24. Toothed wheel 100 meshes in with the toothing of fixed ring 95. Since toothed wheel 100 cooperates with fixed ring 95, the rotating of toothed wheel 100 by first motor 96 rotates mobile ring 24 with respect to fixed ring 95. Motor 96 moves along with mobile ring 24 and thus remains fixed with respect to mobile ring 24 upon rotation thereof. Upon sole rotation of mobile ring 24, there thus is no risk for trocar 14 and first motor 96 to collide. It is thus possible to pivot mobile ring 24 by more than 360 degrees.

Figure 4F:
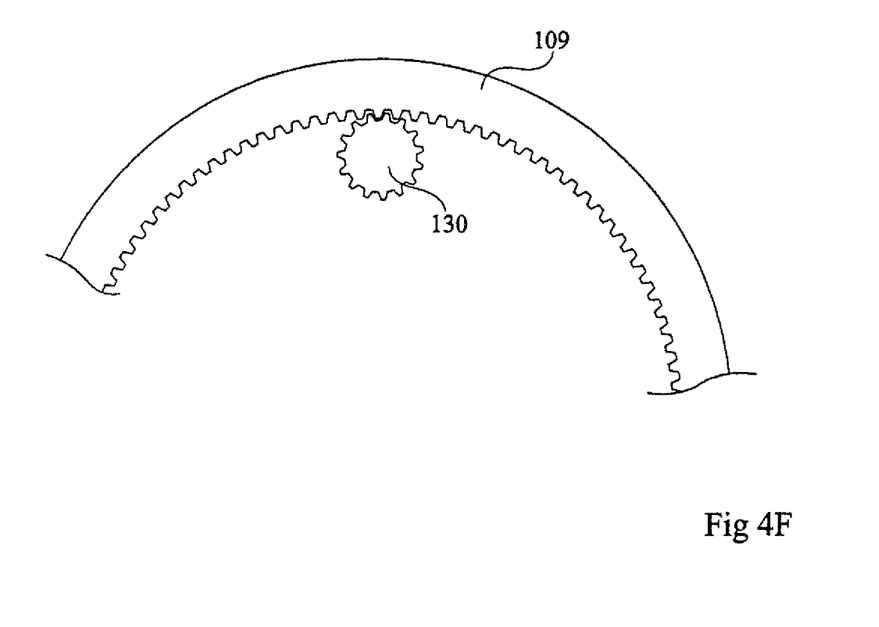

A second electric motor 104 is attached to stirrup 26, on the side of stirrup 26 opposite to mounting flange 90, via a stage 106. The shaft (not visible in the drawings) of second motor 104 is oriented along pivoting axis Γ of stirrup 26. Stage 106 comprises an opening (not visible in the drawings) enabling passing of the shaft of second motor 104. Second motor 104 is controlled and supplied by means not shown, for example, electric wires. A drive element 108 comprises a circular arc 109 having its ends connected by a rectilinear portion 110 attached to mobile ring 24. Drive element 108 substantially extends in a plane perpendicular to the plane containing mobile ring 24. The axis of circular arc 109 corresponds to pivoting axis Γ of stirrup 26. The wall of circular arc 109 opposite to rectilinear portion 110 comprises a toothing shown in FIG. 4F. The shaft of second motor 104 supports a toothed wheel 130 which cooperates with the toothing of circular arc 109 so that, when the toothed wheel is rotated by second motor 104, stirrup 26 is pivoted with respect to mobile ring 24. The toothing is provided inside of drive element 108 for security reasons and to increase the compactness of positioning system 10.

The free end of endoscope 12 comprises a cylindrical stop 112 from which a pin 114 projects. Compression spring 56 bears at one end against cylindrical stop 112 and at the opposite end against trocar 14. A third electric motor 116 is attached to stirrup 26, next to second motor 104, via a stage 118. Stage 118 comprises an opening 120 enabling passing of shaft 122 of third motor 116. Shaft 122 of third motor 116 is oriented along pivoting axis Γ of stirrup 26. Third motor 116 is controlled and supplied by means not shown, for example, by electric wires. A winding cylinder 124 is arranged at the free end of shaft 122. A helical threading (not shown) is formed on the outer surface of winding cylinder 124. A cable 125 (only shown in FIG. 4A) is connected at its ends to pin 114 and to cylinder 124 and wound around cylinder 124. Third electric motor 116 is arranged between second motor 104 and protrusion 92 to avoid for cable 125 to contact second motor 104. When third motor 116 rotates shaft 122, cable 125, guided by the threading of cylinder 124, winds around cylinder 124 and brings cylindrical stop 112 closer to trocar 14. Endoscope 12 then slides in trocar 14 along axis Ω and compresses spring 56. When third motor 116 is no longer actuated, spring. 56 relaxes and brings endoscope 12 back to an idle position. Cylindrical stop 112 may be disassembled from endoscope 12 to enable removal of endoscope 12 from trocar 14. Cylindrical stop 112 may move along with endoscope 12. The cable end connected to pin 114 can then be detached to release endoscope 12 from trocar 14. Stages 106, 118 may be directly integrated to stirrup 26 and/or be provided on a same side of stirrup 26.

The rotating motions of endoscope 12 in trocar 14 around its axis Ω may also be controlled by an actuator.

In FIGS. 4A to 4D, ring-shaped base 18 is maintained on the patient via four curved tongues 126 radially extending from ring-shaped base 18. A support arm, oriented by the surgeon before the beginning of the operation, may be provided to support positioning system 10 and avoid for the entire weight of positioning system 10 to be applied on the patient.

A notch 128 is provided at the level of mobile ring 24, substantially in diametrically opposite position with respect to first electric motor 96. Notch 128 is intended to receive a portion of trocar 14 when the latter is inclined to a maximum with respect to ring-shaped base 18, as shown in FIG. 4B. A maximum inclination angle greater than in the absence of notch 128 has then been achieved. Notch 128 may be replaced by a hollow print performed in mobile ring 24 and the shape of which is complementary to the shape of trocar 14.

In FIGS. 4C and 4D, trocar 14 is shown as inclined with respect to the plane of ring-shaped base 18 to a position where the second and third motors 104, 116 thrust against first motor 96. Trocar 14 being attached to stirrup 26 by mounting flange 90 on the side opposite to second and third motors 104, 106, it can then be easily released from positioning system 10. Stirrup 26 being maintained in a thrust position against first motor 96, an obstacle-free region 130 is freed between stirrup 26 and ring-shaped base 18, enabling removal of positioning system 10 while leaving in place trocar 14, the dimensions of the obstacle-free region being sufficient to enable removal of positioning system 10 despite the presence of protuberance 92 and cylindrical stop 112.

The system according to the present invention has many advantages

First, the positioning system according to the present invention takes up a small volume, is formed of a relatively simple structure, and has a small weight. As an example, the applicant has formed a positioning system according to the present invention comprised in a cylinder with a 70-mm diameter and with a 75-mm height, with a weight approximately smaller than 600 g (to which must be added the weights of the endoscope, of the trocar, and possibly of the camera). Several positioning systems according to the present invention may thus be placed simultaneously on a patient's body, each system enabling positioning an observation and/or intervention device.

Second, the pivoting axis of the endoscope with respect to the patient's body is substantially tangent to the patient's body, which enables reducing to a minimum the dimensions of the incision to be performed for the introduction of the trocar and of the endoscope into the patient's body.

Third, the positioning system according to the present invention enables obtaining movement angle of the endoscope between axes Ω and Δ greater than 80.degree., with a 0.5.degree. accuracy and a pivoting axis on the order of 25.degrees, and a sliding of endoscope 12 in trocar 14 along axis Ω. greater than 200 mm, with a 5-mm accuracy and a sliding speed on the order of 25 mm/s.

Fourth, the system enables applying no force on the patient's abdomen at the level of the incision through which the endoscope penetrates into the abdomen.

Fifth, only three actuators are necessary to control the endoscope displacements. This enables simple and accurate control of the actuators.

Sixth, the system according to the present invention may easily be arranged on the patient's body and removed from the patient's body while maintaining in place the trocar and the endoscope.

Of course, the present invention is likely to have various alterations and modifications which will occur to those skilled in the art. In particular, the electric motors may be replaced with any type of actuators. Further, the system according to the present invention enables positioning devices other than an endoscope. It may be, for example, a separator, a clip, etc.

What is claimed is:

1. A system for controlling with respect to a patient's body an extremity of an observation and/or intervention device having a portion penetrating into the patient's body, comprising:

a base adapted to be disposed over the patient's body;
first means for supporting and orienting the device formed of a first portion rotatably assembled on the base according to a connection with one degree of freedom, and of a second portion rotatably assembled on the first portion according to a connection with one degree of freedom;
a first actuator for actuating the first portion with respect to the base, and a second actuator for actuating the second portion with respect to the first portion,
wherein at least one of the base and the first portion comprises a surface configured to engage with a complementary drive element coupled to the first actuator; and
wherein at least one of the first portion and the second portion comprises a surface configured to engage with a complementary drive element coupled to the second actuator.

2. The system of claim 1, wherein the base delimits a circular opening around the device and in which the first portion is a mobile ring with an axis substantially perpendicular to the patient's body and with an inner diameter substantially corresponding to the circular opening, the mobile ring being rotatably assembled on the base around its axis.

3. The system of claim 2, wherein the rotation motion of the mobile ring with respect to the base is controlled by the first actuator attached to the mobile ring, the first actuator extending to be substantially parallel to the mobile ring axis.

4. The system of claim 2, wherein the second portion comprises a head coupled to the device prolonging at least in an arm pivotally assembled on the mobile ring along an axis substantially tangent to the patient's body.

5. The system of claim 4, wherein the pivoting motion of the arm with respect to the mobile ring is controlled by the second actuator attached to the second portion and extending to be substantially parallel to the pivoting axis of the arm with respect to the mobile ring.

6. The system of claim 4, wherein the device extends substantially longitudinally along a direction perpendicular to the pivoting axis of the arm with respect to the mobile ring and in which the device is movably assembled with respect to the second portion, to slide along said direction, the device sliding with respect to the second portion being controlled by a third actuator attached to the second portion and extending to be substantially parallel to the pivoting axis of the arm with respect to the mobile ring.

7. The system of claim 4, wherein the device extends substantially longitudinally along a direction perpendicular to the pivoting axis of the arm with respect to the mobile ring and in which the device is movably assembled with respect to the second portion to slide along said direction.

8. The system of claim 1, wherein the device is movably assembled on the second portion according to a connection with one degree of freedom.

9. The system of claim 1, wherein the surface of at least one of the base and the first portion comprises a toothed configuration that engages with the complementary drive element.

10. The system of claim 9, wherein the base comprises the toothed configuration, and the first actuator is attached to the first portion such that the first actuator remains stationary with respect to the first portion when rotating with respect to the base.

11. The system of claim 1, wherein the first portion is rotatably assembled on the base to rotate around a first axis, the second portion is rotatably assembled on the first portion to rotate around a second axis, said second axis being perpendicular to the first axis, and the device is configured for translational movement with respect to the second portion along a third axis, said third axis being perpendicular to the second axis, wherein the first axis, the second axis and the third axis substantially concur at a same point.

12. The system of claim 1, wherein the surface configured to engage with the complementary drive element coupled to the second actuator comprises a circular arc.

13. The system of claim 12, wherein the second actuator is displaced around the inner wall of the circular arc as the second portion is pivoted with respect to the first portion.

14. The system of claim 12, wherein ends of the circular arc are connected by a rectilinear portion.

15. The system of claim 14, wherein the rectilinear portion is attached to the first portion.

16. The system of claim 14, wherein an inner wall of the circular arc opposite the rectilinear portion comprises a toothed surface.

17. A system for controlling with respect to a patient's body an extremity of an observation and/or intervention device having a portion penetrating into the patient's body, comprising:
a base adapted to be disposed over the patient's body;
first means for supporting and orienting the device formed of a first portion rotatably assembled on the base according to a connection with one degree of freedom, and of a second portion rotatably assembled on the first portion according to a connection with one degree of freedom;
a first actuator for actuating the first portion with respect to the base, and a second actuator for actuating the second portion with respect to the first portion,
wherein at least one of the base and the first portion comprises a surface configured to engage with a complementary drive element coupled to the first actuator,
wherein the base delimits a circular opening around the device and in which the first portion is a mobile ring with an axis substantially perpendicular to the patient's body and with an inner diameter substantially corresponding to the circular opening, the mobile ring being rotatably assembled on the base around its axis,
wherein the second portion comprises a head coupled to the device prolonging at least in an arm pivotally assembled on the mobile ring along an axis substantially tangent to the patient's body, and
wherein at least one of the first portion and the second portion comprises a surface configured to engage with a complementary drive element coupled to the second actuator.

18. The system of claim 17, wherein the base comprises a toothed surface, and the first actuator is attached to the first portion such that the first actuator remains stationary with respect to the first portion when rotating with respect to the base.

19. The system of claim 17, wherein the surface configured to engage with the complementary drive element coupled to the second actuator comprises a toothed portion arranged in an arc such that as the second portion is pivoted with respect to the first portion, the second actuator is displaced around the toothed portion.

* * * * *

UNITED STATES PATENT AND TRADEMARK OFFICE
CERTIFICATE OF CORRECTION

PATENT NO. : 9,643,325 B2
APPLICATION NO. : 14/087724
DATED : May 9, 2017
INVENTOR(S) : Peter Berkelman et al.

It is certified that error appears in the above-identified patent and that said Letters Patent is hereby corrected as shown below:

On the Title Page

Item (75), the name of the second inventor should be "Jean Arnault"

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*